United States Patent [19]

Hageman

[11] 4,375,434

[45] Mar. 1, 1983

[54] PROCESS FOR 6'-AMINO-PENICILLANOYLOXYMETHYL PENICILLANATE 1,1-DIOXIDE

[75] Inventor: David L. Hageman, Colchester, Conn.

[73] Assignee: Pfizer Inc., New York, N.Y.

[21] Appl. No.: 390,465

[22] Filed: Jun. 21, 1982

[51] Int. Cl.$^3$ ............................................ C07D 499/04
[52] U.S. Cl. .............................. 260/245.2 R; 424/270; 424/271; 260/239.1
[58] Field of Search ...................... 260/245.2 R, 239.1; 424/270, 271

[56] References Cited

U.S. PATENT DOCUMENTS 4,244,951  1/1981  Bigham ............................... 424/250

FOREIGN PATENT DOCUMENTS 2044255  10/1980  United Kingdom .

OTHER PUBLICATIONS

Dane and Dockner, Angewandte Chemie, Int. Edn. Eng., 3,439, (1964).

Dane and Dockner, Chem. Ber., 98, 789, (1965).

*Primary Examiner*—Nicholas S. Rizzo
*Attorney, Agent, or Firm*—Charles J. Knuth; Albert E. Frost; J. Trevor Lumb

[57] ABSTRACT

6'-Aminopenicillanoyloxymethyl penicillanate 1,1-dioxide is prepared by a two-step procedure. The first step consists of coupling a salt of a 6-(protected amino)-penicillanic acid with a halomethyl, an alkylsulfonyloxymethyl or an arylsulfonyloxymethyl ester of penicillanic acid 1,1-dioxide, to give a 6'-(protected amino)-penicillanoyloxymethyl penicillanate 1,1-dioxide, wherein the protection at the 6-position has been achieved by coupling the 6-aminopenicillanic acid with a beta-dicarbonyl compound. The second step consists of removal of the protecting group on the 6'-amino group, using aqueous acid. 6'-Aminopenicillanoyloxymethyl penicillanate 1,1-dioxide is a chemical intermediate for preparing antibacterial agents. Also claimed are the 6'-(protected amino)penicillanoyloxymethyl penicillanate 1,1-dioxide compounds used as intermediates in the process of this invention.

6 Claims, No Drawings

PROCESS FOR 6'-AMINO-PENICILLANOYLOXYMETHYL PENICILLANATE 1,1-DIOXIDE

BACKGROUND OF THE INVENTION

U.S. Pat. No. 4,244,951 discloses a series of 6'-acylaminopenicillanoyloxymethyl penicillanate 1,1-dioxides of the formula I:

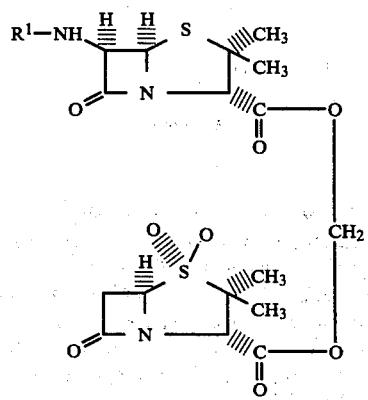

wherein R¹ represents certain acyl groups, said compounds of formula I being of value as antibacterial agents.

One method disclosed in U.S. Pat. No. 4,244,951 for the preparation of said antibacterial agents of formula I comprises acylation of the corresponding compound of formula I, wherein R¹ is hydrogen (6'-aminopenicillanoyloxymethyl penicillanate 1,1-dioxide). In turn, it is disclosed that 6'-aminopenicillanoyloxymethyl penicillanate 1,1-dioxide can be prepared by coupling a salt of a 6-(protected-amino)penicillanic acid compound of the formula

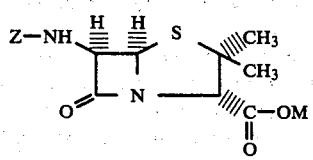

wherein Z is an amino protecting group and M is a carboxylate salt forming cation, with a compound of the formula

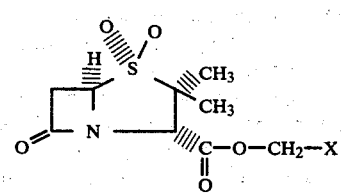

wherein X is a good leaving group, followed by removal of the protecting group. Groups which are disclosed as being useful for the group Z are the benzyloxycarbonyl group, the 4-nitrobenzyloxycarbonyl group and the 2,2,2-trichloroethoxycarbonyl group.

However, it has now been discovered that the aforesaid process for the preparation of the compound of the formula I, wherein R¹ is hydrogen, can be improved by using certain alternate groups for protection of the 6-amino group in the 6-aminopenicillanic acid, i.e. the group Z. Specifically, said process for the preparation of the compound of formula I, wherein R¹ is hydrogen, can be improved by using for Z certain groups obtained by reacting 6-aminopenicillanic acid with certain beta-dicarbonyl compounds.

Accordingly, it is an object of this invention to provide an improved process for the preparation of the compound of the formula I, wherein R¹ is hydrogen, which uses certain alternate protecting groups.

SUMMARY OF THE INVENTION

This invention provides a new process for the preparation of the compound of the formula

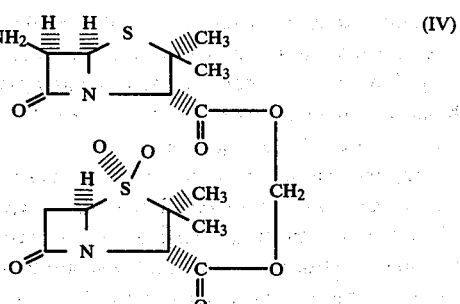

or an acid-addition salt thereof, which comprises:

(i) contacting a compound of the formula

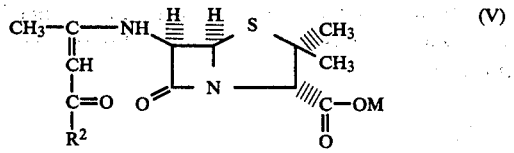

with from 0.5 to 1.5 molar equivalents of a compound of the formula

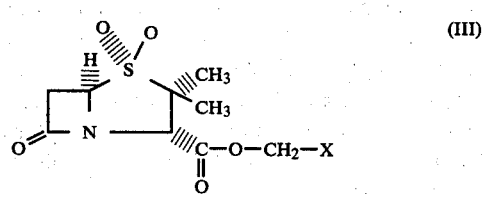

in a reaction-inert organic solvent, at a temperature in the range from 0°–60° C., to give a compound of the formula

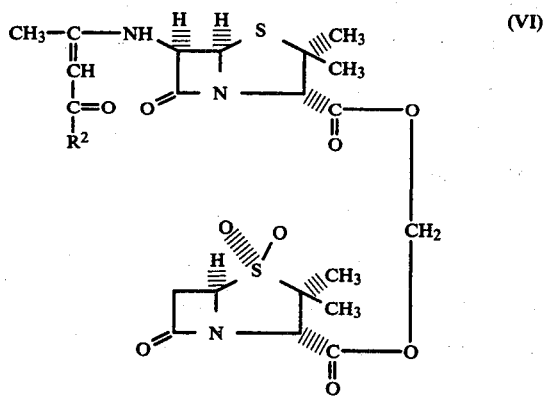

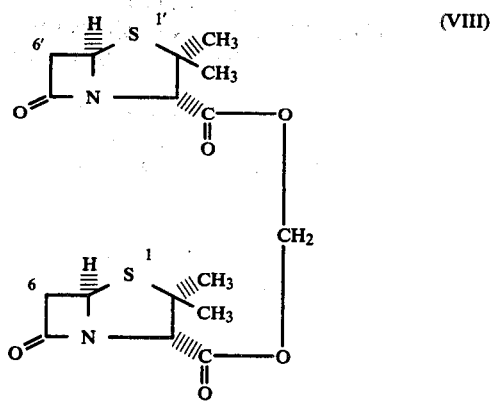

and (ii) exposing the product of step (i) to aqueous or partially aqueous reaction conditions, at a pH in the range from 0.5 to 3.0, at a temperature in the range from 0° to 30° C., until conversion to an acid-addition salt of the compound of formula IV is substantially complete;

wherein $R^2$ is selected from the group consisting of alkyl having 1 to 3 carbons, alkoxy having 1 to 3 carbons and phenyl, M is a carboxylate salt forming cation and X is a good leaving group.

Preferred values for $R^2$ are said alkoxy groups, particularly methoxy; preferred values for M are tetraalkylammonium groups, particularly tetra-n-butylammonium groups; and preferred values for X are chloro, bromo and iodo, particularly iodo.

Also within the scope of this invention are the novel intermediates of formula VI, wherein $R^2$ is as defined previously.

DETAILED DESCRIPTION OF THE INVENTION

This invention relates to derivatives of penicillanic acid, which is represented by the following structural formula

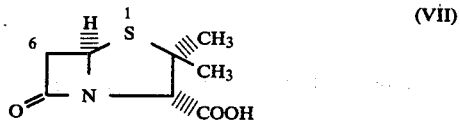

In formula VII, broken line attachment of a substituent to the bicyclic nucleus indicates that the substituent is below the plane of the bicyclic nucleus. Such a substituent is said to be in the alpha-configuration. Conversely, solid line attachment of a substituent to the bicyclic nucleus indicates that the substituent is attached above the plane of the nucleus. This latter configuration is referred to as the beta-configuration.

Using this system, the compounds of formulae I, IV and VI are named as derivatives of penicillanoyloxymethyl penicillanate (VIII), in which primed and unprimed locants are used to distinguish between the two ring systems, viz.:

Step (i) of the present invention involves coupling a compound of the formula V with a compound of formula III, to give a compound of formula VI.

In the compound of formula V, $R^2$ is selected from the group consisting of alkyl having 1 to 3 carbons, alkoxy having 1 to 3 carbons and phenyl, and M is a carboxylate salt forming cation. A wide variety of cations can be used for M, but typical salts which are used are alkali metal salts, such as sodium and potassium salts; alkaline earth metal salts, such as barium and calcium salts; tertiary amine salts, such as trialkylamine salts having 1 to 6 carbons in each alkyl group, N,N-dimethylaniline, pyridine, quinoline, isoquinoline, N-methylmorpholine, N-methylpiperidine, N-methylpyrrolidine and N,N-dimethylpiperazine; and tetraalkylammonium salts having one to six carbons in each alkyl group, such as tetra-n-butylammonium salts.

In the compound of formula III, a variety of leaving groups can be used for X. However, particularly useful groups are chloro, bromo, iodo, alkylsulfonyloxy having from one to four carbon atoms, benzenesulfonyloxy and toluenesulfonyloxy.

The compounds of formulae V and III are normally contacted in a reaction-inert organic solvent at a temperature in the range from 0° to 60° C., and preferably from 20° to 30° C. A wide variety of solvents can be used, the major requirements for said solvent being that it does not adversely interact with either of the starting reagents or the product, and that it substantially dissolves at least one of the starting materials. Accordingly, typical solvents which can be used are low-molecular weight ketones such as acetone and methyl ethyl ketone; low-molecular weight esters, such as ethyl acetate and butyl acetate; low-molecular weight chlorinated hydrocarbons, such as dichloromethane and chloroform; acetonitrile; tertiary amides such as N,N-dimethylformamide, N,N-dimethylacetamide and N-methylpyrrolidone; hexamethylphosphoramide; and mixtures of these solvents. However, when using a compound of formula III in which X is one of the less reactive leaving groups such as chloro, and/or a compound of formula V in which M is a metal ion, it is preferable to use a relatively polar solvent, i.e. one of the aforesaid tertiary amides or hexamethylphosphoramide.

In step (i) of the process, as regards the ratio of the reactants, the compound of formula V is usually reacted with from 0.5 to 1.5 molar equivalents, and preferably about one molar equivalent, of a compound of formula III.

Step (i) of the process of this invention is normally substantially complete in a reaction time from a few minutes to several hours, e.g. 24 hours.

The compound of formula VI can be isolated in conventional fashion. When a water-miscible solvent is used, it is usually sufficient simply to dilute the reaction medium with an excess of water. The product is then extracted into a volatile, water-immiscible solvent, such as ethyl acetate, and then the product is recovered by solvent evaporation. When a water-immiscible solvent is used, it is usually sufficient to wash the solvent with water, and then recover the product by solvent evaporation. The compound of formula VI can be purified by well-known methods, such as chromatography, but due regard must be given to the lability of the beta-lactam ring system and the —C(CH$_3$)=CH—CO—R$^2$ group. Alternatively, the compound of formula VI can be used directly in Step (ii). In a still further option, compound VI can be subjected to Step (ii) without isolation.

Step (ii) of this invention involves removal of the —C(CH$_3$)=CH—CO—R$^2$ group from a compound of formula VI. This is achieved by exposing the compound of the formula VI to an aqueous or partially aqueous solvent system at a pH in the range from 0.5 to 3, at a temperature in the range from 0° to 30° C., until conversion into the acid addition salt of the compound of formula IV is substantially complete. The pH of 0.5 to 3 is achieved simply by adding an acid, and a wide variety of acids can be used. Examples are hydrochloric acid, hydrobromic acid, perchloric acid, nitric acid, sulfuric acid, trifluoroacetic acid, trichloroacetic acid and sulfonic acids, such as alkanesulfonic acid having 1 to 6 carbons, benzenesulfonic acid, a toluenesulfonic or a napthalenesulfonic acid.

If desired, a co-solvent can be added during Step (ii) of this invention. The major requirements of said co-solvent are that it does not adversely interact with either the compound of formula VI or IV and that it is at least partially miscible with water. Typical co-solvents are low-molecular weight ketones, such as acetone; low-molecular weight ethers such as tetrahydrofuran and 1,2-dimethoxyethane; tertiary amides, such as N,N-dimethylformamide, N,N-dimethylacetamide and N-methylpyrrolidone; and acetonitrile.

Step (ii) is usually complete within an hour, and the compound of formula IV is isolated by conventional means. When a volatile co-solvent has been used, usually it is sufficient simply to remove the co-solvent by evaporation in vacuo, followed by removal of the CH$_3$—CO—CH$_2$—CO—R$^2$ compound formed as a by-product by extraction into a volatile, water-immiscible organic solvent such as diethyl ether. Lyophilization of the remaining aqueous solution then affords the compound of formula IV as a salt corresponding to the acid which has been used to render the original reaction medium acidic. Alternatively, the pH of the final aqueous solution can be raised to 7 to 10, and then extraction with a volatile, water-immiscible organic solvent, followed by evaporation of the extract, affords the compound of formula IV in the free base form.

The compound of formula IV prepared according to the process of this invention can be purified by standard methods for penicillin compounds, such as chromatography.

The compounds of formula V are prepared by reaction of 6-aminopenicillanic acid with the appropriate beta-dicarbonyl compound of the formula CH$_3$—CO—CH$_2$—CO—R$^2$, according to standard procedures. Dane and Dockner, *Angewandte Chemie* (International Edition in English) 3, 439 (1964); *Chemische Berichte der Deutschen Chemischen Gesellschaft*, 98, 789 (1965).

The compounds of formula III are known from U.S. Pat. No. 4,244,951.

As indicated hereinbefore, the compound of formula V can be acylated to provide useful anti-bacterial agents. Methods for carrying out this acylation are taught in U.S. Pat. No. 4,244,951.

The following examples and preparations are being provided solely for the purpose of further illustration. Proton nuclear magnetic resonance (NMR) spectra were measured as solutions in deuterochloroform (CDCl$_3$), and $^{13}$C NMR spectra were measured as solutions in perdeutero dimethyl sulfoxide (DMSO-d$_6$), and peak positions are recorded in parts per million (ppm) downfield from tetramethylsilane. The following abbreviations for peak shapes are used: s, singlet; d, doublet; dd, doublet or doublets; t, triplet; and m, multiplet. Infrared (IR) spectra were measured as potassium bromide discs, and the position of significant absorption bands are reported in cm$^{-1}$.

EXAMPLE 1

6'-Aminopenicillanoyloxymethyl Penicillanate 1,1-Dioxide

To a stirred solution of 256 mg of 6'-([1-methyl-2-methoxycarbonylvinyl]amino)penicillanoyloxymethyl penicillanate 1,1-dioxide in a few milliliters of acetone was added 91 mg of 4-toluenesulfonic acid monohydrate. Stirring was continued for 20 minutes and then the acetone was removed by evaporation in vacuo. The residue was partitioned between diethyl ether and water at pH 2.0, and the layers were separated. The diethyl ether layer was removed and the aqueous layer was again extracted with diethyl ether. To the resulting aqueous layer was added chloroform and the pH was adjusted to 8.5. The chloroform layer was removed, dried with sodium sulfate and evaporated in vacuo. This afforded 96 mg of the title compound.

The NMR spectrum of the product (CDCl$_3$) showed absorptions at 1.45 (s, 3H), 1.53 (s, 3H), 1.62 (s, 3H), 1.67 (s, 3H), 1.88 (s, 2H), 3.47 (m, 2H), 4.42 (m, 2H), 4.6 (m, 2H), 5.46 (d, 1H) and 5.87 (m, 2H) ppm.

EXAMPLE 2

The following compounds are treated with 4-toluenesulfonic acid monohydrate, according to the procedure of Example 1:
  6'-([1-methyl-2-ethoxycarbonylvinyl]amino)-penicillanoyloxymethyl penicillanate 1,1-dioxide,
  6'-([1-methyl-2-isopropoxycarbonylvinyl]amino)-penicillanoyloxymethyl penicillanate 1,1-dioxide,
  6'-([1-methyl-2-acetylvinyl]amino)penicillanoyloxymethyl penicillanate 1,1-dioxide,
  6'-([1-methyl-2-butyrylvinyl]amino)penicillanoyloxymethyl penicillanate 1,1-dioxide and
  6'-([1-methyl-2-benzoylvinyl]amino)penicillanoyloxymethyl penicillanate 1,1-dioxide.

In each case, this affords 6'-aminopenicillanoyloxymethyl penicillanate 1,1-dioxide.

EXAMPLE 3

6'-Aminopenicillanoyloxymethyl Penicillanate 1,1-Dioxide

To a rapidly stirred mixture of 1.0 g of 6'-([1-methyl-2-methoxycarbonylvinyl]amino)penicillanoyloxymethyl penicillanate 1,1-dioxide, 5 ml of water and 10 ml of tetrahydrofuran is added 1 N hydrochloric acid, dropwise, until a pH of 2.0 is achieved. The addition of 1 N hydrochloric acid is continued, with stirring, to maintain the pH at 2.0 until it is no longer necessary to add acid to keep the pH at 2.0. Stirring is continued for a further 15 minutes, and then the bulk of the tetrahydrofuran is removed by evaporation in vacuo. Water (30 ml) and diethyl ether (30 ml) are added and the layers are separated. Chloroform (30 ml) is added to the aqueous phase, and the pH is raised to 8.5. The layers are separated and the aqueous layer is extracted further with chloroform. The combined chloroform layers are dried ($Na_2SO_4$) and evaporated in vacuo to give the title compound.

EXAMPLE 4

6'-([1-Methyl-2-methoxycarbonylvinyl]amino)-penicillanoyloxymethyl Penicillanate 1,1-Dioxide A solution of 5.57 g of tetra-n-butylammonium 6-([1-methyl-2-methoxycarbonylvinyl]amino)penicillanate and 3.53 g of iodomethyl penicillanate 1,1-dioxide in 30 ml of acetone was stored overnight. The acetone was removed by evaporation in vacuo to give 5.5 g of the title compound. This material was purified by chromatography on silica gel, eluting with 1:4 ethyl acetate-dichloromethane. This afforded 1.0 g of purified product.

The NMR spectrum of the purified product ($CDCl_3$) showed absorptions at 1.45 (s, 3H), 1.55 (s, 3H), 1.62 (s, 3H), 1.7 (s, 3H), 2.03 (s, 3H), 3.47 (m, 2H), 3.65 (s, 3H), 4.4 (s, 1H), 4.5 (s, 1H), 4.62 (m, 2H), 5.15 (dd, 1H), 5.57 (d, 1H), and 5.9 (m, 2H) ppm.

EXAMPLE 5

Reaction of the following salts:
sodium 6-([1-methyl-2-methoxycarbonylvinyl]-amino)penicillanate,
potassium 6-([1-methyl-2-methoxycarbonylvinyl]-amino(penicillanate,
tetra-n-butylammonium 6-([1-methyl-2-ethoxycarbonylvinyl]amino)penicillanate,
sodium 6-([1-methyl-2-ethoxycarbonylvinyl]amino)-penicillanate,
tetra-n-butylammonium 6-([1-methyl-2-isopropoxycarbonylvinyl]amino)penicillanate,
sodium-6-([1-methyl-2-acetylvinyl]amino)penicillanate,
tetra-n-butylammonium 6-([1-methyl-2-butyrylvinyl]-amino)penicillanate and
potassium 6-([1-methyl-2-benzoylvinyl]amino)-penicillanate,
respectively, with the following penicillanic acid 1,1-dioxide derivatives:
iodomethyl penicillanate 1,1-dioxide,
methylsulfonyloxymethyl penicillanate 1,1-dioxide,
butylsulfonyloxymethyl penicillanate 1,1-dioxide,
benzenesulfonyloxymethyl penicillanate 1,1-dioxide,
bromomethyl penicillanate 1,1-dioxide,
4-toluenesulfonyloxymethyl penicillanate 1,1-dioxide,
iodomethyl penicillanate 1,1-dioxide and
bromomethyl penicillanate 1,1-dioxide,
respectively, according to the procedure of Example 4, affords the following compounds:
6'-([1-methyl-2-methoxycarbonylvinyl]amino)-penicillanoyloxymethyl penicillanate 1,1-dioxide,
6'-([1-methyl-2-methoxycarbonylvinyl]amino)-penicillanoyloxymethyl penicillanate 1,1-dioxide,
6'-([1-methyl-2-ethoxycarbonylvinyl]amino)-penicillanoyloxymethyl penicillanate 1,1-dioxide,
6'-([1-methyl-2-ethoxycarbonylvinyl]amino)-penicillanoyloxymethyl penicillanate 1,1-dioxide,
6'-([1-methyl-2-isopropoxycarbonylvinyl]amino)-penicillanoyloxymethyl penicillanate 1,1-dioxide,
6'-([1-methyl-2-acetylvinyl]amino)penicillanoyloxymethyl penicillanate 1,1-dioxide,
6'-([1-methyl-2-butyrylvinyl]amino)penicillanoyloxymethyl penicillanate 1,1-dioxide and
6'-([1-methyl-2-benzoylvinyl]amino)penicillanoyloxymethyl penicillanate 1,1-dioxide, respectively.

PREPARATION 1

Tetra-n-butylammonium 6-([1-methyl-2-methoxycarbonylvinyl[amino)penicillanate To a rapidly stirred suspension of 2.16 g of 6-aminopenicillanic acid in 50 ml of chloroform was added 6.55 ml of 40% aqueous tetra-n-butylammonium hydroxide. Stirring was continued for 5 minutes and then the layers were separated. The chloroform layer was dried and evaporated in vacuo, and then the residue was dissolved in 3.2 ml of methyl acetoacetate. This solution was heated at 60° C. for 15 minutes and then cooled. The residue was triturated with 2:1 diethyl ether-hexane. It was then dissolved in chloroform and evaporated in vacuo several times. This finally afforded 5.57 g of the title product.

The NMR spectrum of the title compound ($CDCl_3$) showed absorptions at 1.03 (m), 1.57 (m), 1.97 (s, 3H), 3.3 (m), 3.62 (s, 3H), 4.2 (s, 1H), 4.72 (s, 1H), 4.93 (dd, 1H) and 5.28 (d, 1H) ppm.

PREPARATION 2

Conversion of 6-aminopenicillanic acid to its tetra-n-butylammonium salt, followed by reaction with ethyl acetoacetate, isopropyl acetoacetate and 1,3-heptanedione, respectively, according to the procedure of Preparation 1, affords the following compounds:
tetra-n-butylammonium 6-([1-methyl-2-ethoxycarbonylvinyl]amino)penicillanate,
tetra-n-butylammonium 6-([1-methyl-2-isopropoxycarbonylvinyl]amino)penicillanate and
tetra-n-butylammonium 6-([1-methyl-2-butyrylvinyl-]amino)penicillanate, respectively.

PREPARATION 3

Sodium 6-([1-Methyl-2-methoxycarbonylvinyl]amino)penicillanate

To a stirred suspension of 2.16 g of 6-aminopenicillanic acid in 20 ml of methanol is added 0.54 g of sodium methoxide. Stirring is continued for 15 minutes and then the bulk of the solvent is removed by evaporation in vacuo. To the stirred residue is added 5 ml of methyl acetoacetate and stirring is continued for one hour at room temperature and 50° C. for 5 hours. To the cooled reaction mixture is added 1:1 diethyl ether-hexane and the solid is recovered by filtration to give the title compound.

PREPARATION 4

Formation of the appropriate salt of 6-aminopenicillanic acid followed by reaction with methyl acetoacetate, ethyl acetoacetate, acetylacetone and benzoylacetone, respectively, according to the procedure of Preparation 3, affords the following compounds:
potassium 6-([1-methyl-2-methoxycarbonylvinyl]amino)penicillante,
sodium 6-([1-methyl-2-ethoxycarbonylvinyl]amino)penicillanate,
sodium 6-([1-methyl-2-acetylvinyl]amino)penicillanate and
potassium 6-([1-methyl-2-benzoylvinyl]amino)penicillanate, respectively.

PREPARATION 5

Chloromethyl Penicillanate 1,1-Dioxide

A mixture of 4.66 g of penicillanic acid 1,1-dioxide, 50 ml of dichloromethane and 35 ml of water was treated with sufficient tetra-n-butylammonium hydroxide (40% in water) to give a pH of 6.0. The dichloromethane layer was separated and the aqueous phase extracted with fresh dichloromethane (2×50 ml). The organic layers were combined, dried over sodium sulfate and concentrated to give 10.1 g of the tetra-n-butylammonium salt of penicillanic acid 1,1-dioxide.

The above tetra-n-butylammonium penicillanate 1,1-dioxide was added to 50 ml of chloroiodomethane and the reaction mixture allowed to stir at ambient temperature overnight. The reaction mixture was concentrated to half volume in vacuo, and chromatographed on 200 g of silica gel using ethyl acetate/hexane as the eluant, 12 ml cuts being taken every 30 sec. Fractions 41-73 were combined and concentrated to dryness to give 3.2 g of the title compound.

The NMR spectrum (CDCl$_3$) showed absorptions at 1.5 (s, 3H), 1.66 (s, 3H), 3.42 (d, 2H), 4.38 (s, 1H), 4.6 (t, 1H) and 5.7 (dd, 2H) ppm.

PREPARATION 6

Iodomethyl Penicillanate 1,1-Dioxide

To a solution of 7.9 g of chloromethyl penicillanate 1,1-dioxide in 100 ml of dry acetone maintained under a nitrogen atmosphere was added 21.0 g of sodium iodide, and the reaction mixture was allowed to stir overnight at room temperature. The reaction mixture was concentrated in vacuo, and the residue was dissolved in 150 ml ethyl acetate and 150 ml water. The organic layer was separated and the aqueous layer was extracted with fresh ethyl acetate. The organic extracts were combined, washed with water (1×500 ml) and brine (1×50 ml) and dried over sodium sulfate. Removal of the solvent gave 10.5 g of the title product, m.p 100°-102° C.

The NMR spectrum (CDCl$_3$) showed absorptions at 1.55 (s, 3H), 1.68 (s, 3H), 3.5 (d, 2H), 4.4 (s, 1H), 4.65 (t, 1H) and 6.0 (dd, 2H) ppm.

PREPARATION 7

6'-(2-Amino-2-phenylacetamido)penicillanoyloxymethyl Penicillanate 1,1-Dioxide Hydrochloride To a solution of ca. 1.36 g of 6'-aminopenicillanoyloxymethyl penicillanate 1,1-dioxide in dichloromethane, cooled to −35° C., was added, with stirring, 1.83 ml of N,N-dimethylaniline followed by 0.75 g of 2-amino-2-phenylacetyl chloride hydrochloride. Stirring was continued at −20° C. for 30 minutes and then the reaction mixture was poured, with stirring, into a solution prepared from 0.24 g of sodium bicarbonate and 10 ml of water. Stirring was continued for 10 minutes and then the dichloromethane layer was removed. The aqueous layer was extracted with dichloromethane, and the combined dichloromethane solutions were washed with saturated sodium chloride, dried using sodium sulfate and evaporated in vacuo. The residue was dissolved in ca. 50 ml of dichloromethane and this solution was added slowly to ca. 100 ml of hexane. The solid which precipitated was recovered by filtration to give 1.37 g of crude title product.

This latter product was triturated under ether and then it was dissolved in ca. 25 ml of dichloromethane. The dichloromethane solution was cooled to ca. −70° C. and ca. 30 ml of hexane was added slowly with stirring. Stirring was continued for 10 minutes. The solid was then recovered by filtration to give 1.19 g of the title compound, m.p. 164°-170° C. (dec.).

The NMR spectrum of the product (in DMSO-d$_6$) showed absorptions at 9.4 (d, 1H), 9.0 (broad s, 2H), 7.4 (m, 5H), 5.8 (s, 2H), 5.4 (m, 2H), 5.1 (broad s, 2H), 4.5 (s, 1H), 4.4 (s, 1H), 3.6 (m, 1H), 3.3 (m, 1H), 1.4 (s, 3H) and 1.3 (s, 6H) ppm downfield from tetramethylsilane. The IR spectrum of the product (KBr disc) showed absorptions at 3400, 2950, 1790, 1690, 1320 and 990 cm$^{-1}$. The $^{13}$C proton decoupled NMR spectrum of the product (in DMSO-d$_6$) showed absorptions at 172.406, 171.931, 167.563, 166.131, 165.749, 133.622, 129.649, 129.015, 128.546, 127.873, 81.0634, 69.7087, 67.1798, 63.9624, 62.2723, 60.6689, 58.6824, 54.8879, 37.6945, 30.1372, 26.4151, 19.6717, 17.7702 downfield from tetramethylsilane.

I claim:

1. A process for preparing the compound of the formula

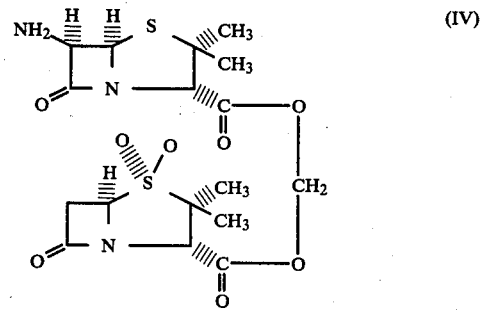

or an acid addition salt thereof, which comprises:
(i) contacting a compound of the formula

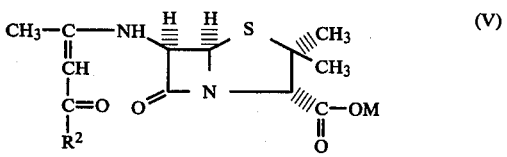

with from 0.5 to 1.5 molar equivalents of a compound of the formula in a reaction-inert organic solvent, at a temperature in the range from 0°-60° C., to give a compound of the formula

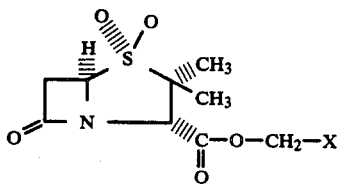

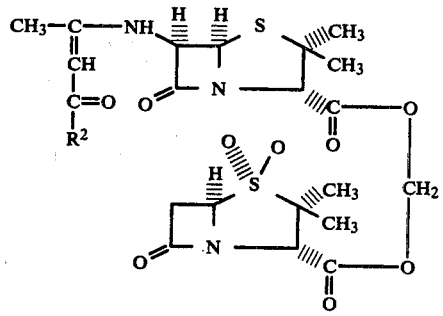

and (ii) exposing the product of step (i) to aqueous or partially aqueous reaction conditions, at a pH in the range from 0.5 to 3.0, at a temperature in the range from 0° to 30° C., until conversion to an acid-addition salt of the compound of formula IV is substantially complete;

wherein $R^2$ is selected from the group consisting of alkyl having 1 to 3 carbons, alkoxy having 1 to 3 carbons and phenyl, M is a carboxylate salt forming cation and X is selected from the group consisting of chloro, bromo, iodo, alkylsulfonyloxy having from 1 to 4 carbons, benzenesulfonyloxy and toluenesulfonyloxy.

2. The process according to claim 1, wherein $R^2$ is said alkoxy.

3. The process according to claim 2, wherein $R^2$ is methoxy.

4. The process according to claim 2 or claim 3, wherein X is chloro, bromo or iodo.

5. The process according to claim 4, wherein X is iodo.

6. The process according to claim 5, wherein M is a tetra-n-butylammonium cation.

* * * * *